United States Patent
Sauer

(10) Patent No.: US 6,632,205 B1
(45) Date of Patent: Oct. 14, 2003

(54) STRUCTURE FORMING A SUPPORT CHANNEL ADJACENT A GLUTEAL FOLD

(75) Inventor: Barbara O. Sauer, Fremont, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 209 days.

(21) Appl. No.: 09/648,160

(22) Filed: Aug. 25, 2000

(51) Int. Cl.$^7$ .................................................. A61F 13/15
(52) U.S. Cl. ......................... 604/385.01; 604/385.12; 604/385.101; 604/385.16
(58) Field of Search ........................ 604/385.12, 385.01, 604/367, 385.101, 378, 379, 380, 385.16

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 5,057,368 A | 10/1991 | Largman et al. |
| 5,069,970 A | 12/1991 | Largman et al. |
| 5,277,976 A | 1/1994 | Hogle et al. |
| 5,306,266 A * | 4/1994 | Freeland .................. 604/385.1 |
| 5,330,459 A * | 7/1994 | Lavon et al. ............ 604/385.1 |
| 5,462,541 A | 10/1995 | Bruemmer et al. |
| 5,466,410 A | 11/1995 | Hills |
| 5,643,241 A * | 7/1997 | Ahr et al. ................. 604/385.1 |
| 5,833,677 A | 11/1998 | Sauer |
| 5,843,056 A | 12/1998 | Good et al. |
| 5,865,824 A * | 2/1999 | Chen et al. .................. 604/378 |
| 5,876,393 A * | 3/1999 | Ahr et al. .................... 604/387 |
| 5,902,297 A | 5/1999 | Sauer |
| 6,022,338 A | 2/2000 | Putzer |
| 6,186,991 B1 * | 2/2001 | Roe et al. ................... 604/361 |
| 6,346,097 B1 * | 2/2002 | Blaney ........................ 604/327 |
| 6,454,750 B1 * | 9/2002 | Vogt et al. ............. 604/385.19 |

* cited by examiner

*Primary Examiner*—Weilun Lo
*Assistant Examiner*—Jacqueline F Stephens
(74) *Attorney, Agent, or Firm*—Pauley Petersen & Erickson

(57) ABSTRACT

A personal care absorbent article, such as an infant diaper, a training pant, an incontinence garment and the like, having a structure for opening a support channel adjacent a gluteal fold when the wearer is in a sitting position. The structure having an expandable element hingedly connected to a compressible element whereby the expandable element forms the support channel upon compression of the compressible element.

18 Claims, 4 Drawing Sheets

STRUCTURE FORMING A SUPPORT CHANNEL ADJACENT A GLUTEAL FOLD

BACKGROUND OF THE INVENTION

1. Field of the Invention

This invention relates to personal care absorbent articles, such as child training pants, disposable diapers, adult incontinence garments and the like, having a structure adapted to expand to form a support channel when a wearer of the personal care absorbent article is in a sitting position. More particularly, this invention relates to a structure having an expandable element which expands to form the support channel when a compressible element hingedly connected thereto is compressed.

2. Description of Prior Art

Conventional personal care absorbent articles, such as disposable diapers and child training pants, employ an absorbent layer positioned between a liquid pervious topsheet and a liquid impervious backsheet to absorb body exudates. These articles typically have elasticized waistbands and legbands to help contain the body exudates and prevent leakage. However, many conventional personal care absorbent articles are not completely leak free.

To help prevent undesirable leakage, some conventional personal care absorbent articles may have compression resistant containment dams which are configured to inhibit the longitudinal flow of fecal material along a surface of the absorbent article contacting the wearer's skin. Such containment dams are positioned within the article so that when the wearer is in a sitting position, the containment dam is positioned along a line where the wearer's buttocks depart from the flat sitting surface.

Other conventional personal care absorbent articles may have an elevating device which provides a spacing between the topsheet and the absorbent layer. The topsheet has an opening and the absorbent layer has a hole to receive and isolate body exudates away from the wearer.

Notwithstanding improvements that have been made, leakage continues to be a problem. Accordingly, there remains a need for personal care absorbent articles which satisfactorily receive and contain body exudates without leakage.

SUMMARY OF THE INVENTION

In response to the discussed difficulties and problems encountered in the prior art, a structure for use in personal care absorbent articles has been discovered which facilitates fecal transport and containment and, in so doing, reduces the potential for leakage.

The disposable absorbent article has an absorbent chassis which defines a front waist region, a back waist region, and a crotch region intermediate to and interconnecting the front waist region and the back waist region. The absorbent chassis includes a rectangular composite structure having a backsheet, a topsheet which is connected to the backsheet in a superposed relation, and an absorbent layer which is located between the backsheet and the topsheet.

A structure is disposed within the crotch region which is suitable for opening a support channel adjacent the gluteal fold of the wearer. Desirably, the structure is positioned between the topsheet and the wearer. The structure comprises an expandable element hingedly connected to a compressible element so that when the compressible element is compressed, typically when the wearer is in a sitting position, the expandable element expands to form the support channel.

When the training pant or the personal care absorbent article is positioned properly on the wearer, the compressible element is positioned adjacent an ischia area corresponding to at least one ischium. The term "ischium" refers to a lower portion of an innominate bone, generally on which the body rests when in a sitting position. When the wearer is in a sitting position, the expandable element is adjacent a target area, and desirably the support channel lies along a longitudinal centerline of the training pant adjacent the gluteal fold. In an expanded configuration, the support channel provides sufficient void space for fecal transport and containment. In one embodiment, a plurality of rib extensions extend transversely across the gluteal fold to form a frame which applies a pressure sufficient to separate the buttocks as the expandable element expands to form the support channel.

The structure is one which is generally resiliently deformable so that it returns to its original shape after the deforming force is removed. Desirably, the structure is a polymer having a high material memory to allow the structure to recover its original configuration. Further, the expandable element must have sufficient strength to withstand the compression force exerted by the ischia area and to separate the buttocks to form the void space and/or support channel for fecal transport and containment. At least a portion of the structure may be covered with a cover material to provide softness and comfort to the absorbent chassis.

BRIEF DESCRIPTION OF THE DRAWINGS

These and other objects and features of this invention will be better understood from the following detailed description taken in conjunction with the drawings wherein.

DEFINITIONS

Figure 2:
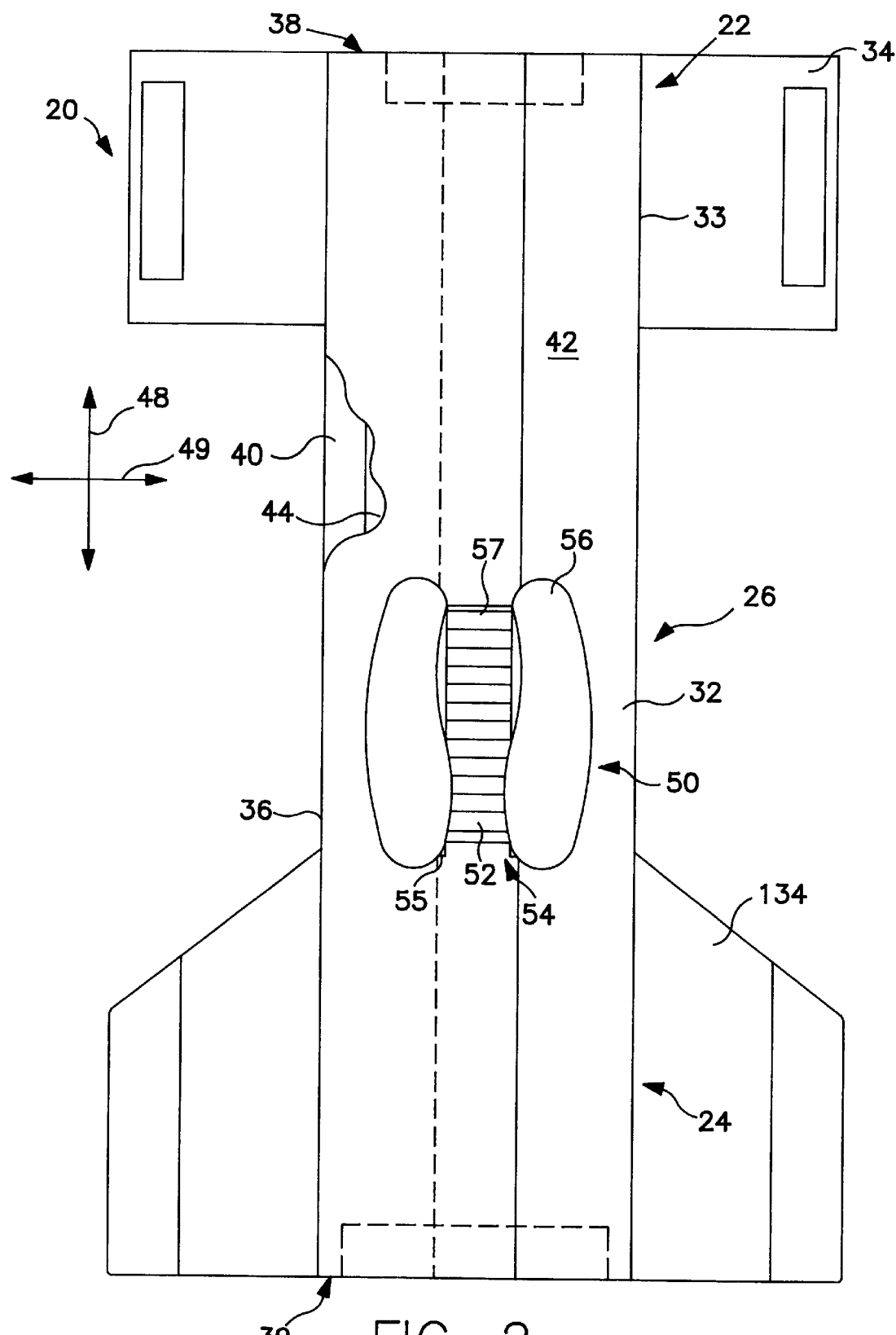
FIG. 2 is a representative plan view of a child's training pant in a flat, uncontracted state, having a structure forming a support channel, in accordance with one embodiment of this invention.

As used herein, "longitudinal", "transverse" and "lateral" have their customary meaning. The longitudinal axis lies in the plane of the article and is generally parallel to a vertical plane that bisects a standing wearer into left and right body halves when the article is worn. The transverse or lateral axis lies in the plane of the article generally perpendicular to the longitudinal axis. The article as illustrated in FIG. 2 is longer in the longitudinal direction than in the transverse direction. The term "z-direction" refers to a direction not within the plane of the article and desirably, but not necessarily, generally perpendicular to the longitudinal direction and the transverse direction.

As used herein, the term "gluteal fold" refers to the somewhat void region between the wearer's buttocks.

As used herein, the term "compression resistance" refers to the compression resistance value determined according to the Compression Resistance Test set forth below.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, atactic, syndiotactic and random symmetries.

As used herein, the term "nonwoven" or "nonwoven web" means a structure of individual fibers or threads which are interlaid, but not in an identifiable repeating manner. Nonwoven webs have been, in the past, formed by a variety of processes such as, for example, meltblowing processes, spunbonding processes, coforming processes, hydroentangling, air-laid and bonded carded web processes.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10 fibers) larger than 7 microns, more particularly, between about 10 and 30 microns. The fibers may also have shapes such as those described in U.S. Pat. No. 5,277,976 to Hogle et al., U.S. Pat. 5,466,410 to Hills, and U.S. Pat. No. 5,069,970 and U.S. Pat. No. 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, are generally smaller than 10 microns in average diameter.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

"Superabsorbent" or "superabsorbent material" refers to a waters-wellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

As used herein, the term "personal care article" or "personal care absorbent article" means feminine hygiene products, diapers, training pants, absorbent underpants, adult incontinence products and wound care products, including bandages.

These terms may be defined with additional language in the remaining portions of the specification.

DETAILED DESCRIPTION OF THE PRESENTLY PREFERRED EMBODIMENTS

The principles of the present invention can be incorporated into any suitable disposable personal care absorbent article. Examples of such suitable articles include infant diapers, training pants, feminine hygiene products, incontinence products, other personal care or health care garments, and the like. For ease of explanation, the description hereafter will be in terms of a child's training pant.

Figure 1:
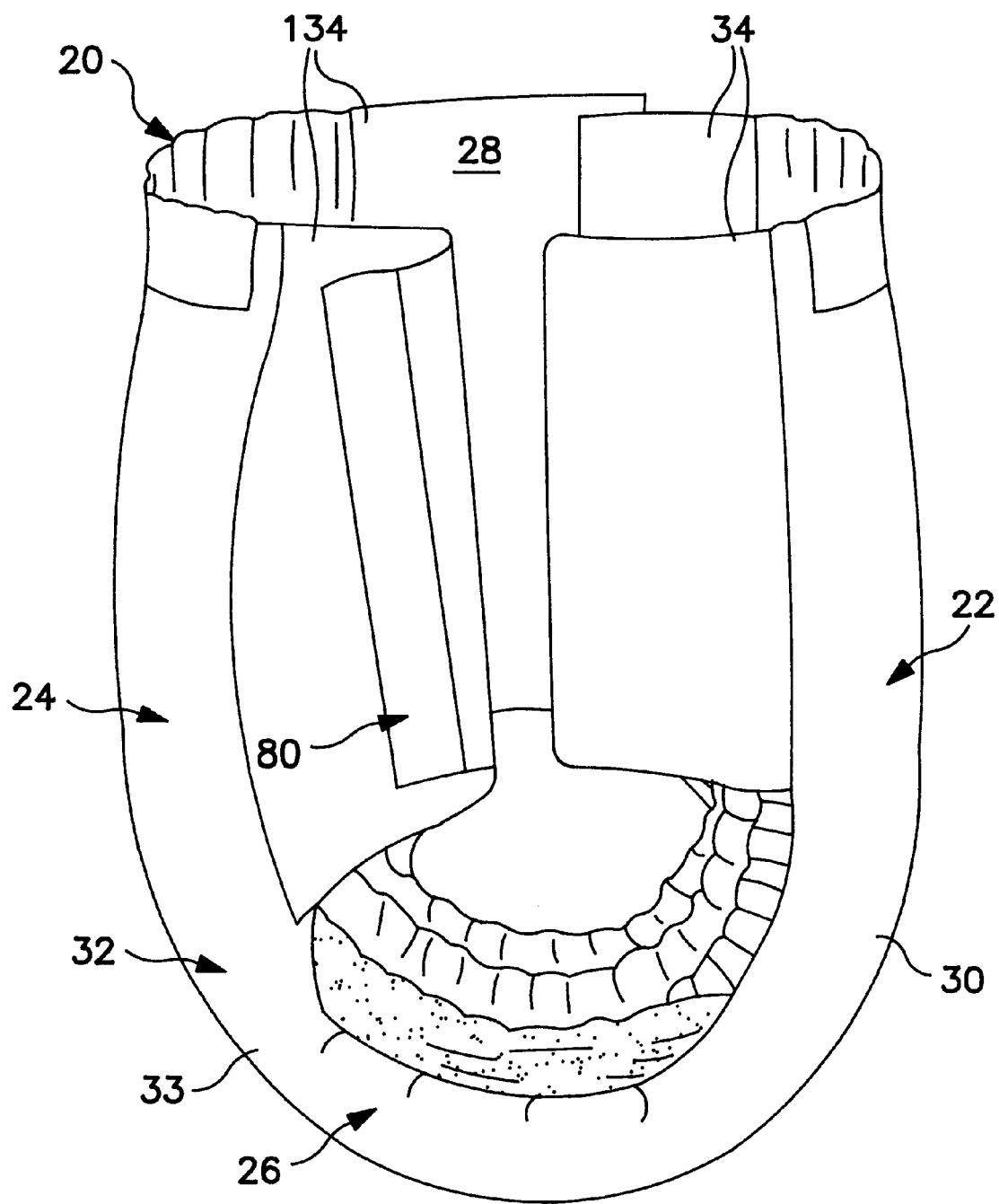
FIG. 1 is a representative perspective view of a child's training pant in a partially fastened position, in accordance with one embodiment of this invention.

As shown in FIG. 1, a disposable absorbent article, such as a training pant 20, comprises an absorbent chassis 32 and a fastening system 80. The absorbent chassis 32 defines a front waist section or region 22, a back waist section or region 24, and a crotch section or region 26 intermediate to and interconnecting the front waist region 22 and the back waist region 24. The front waist region 22 comprises the portion of the training pant 20 which, when worn, is positioned on the front of the wearer while the back waist region 24 comprises the portion of the training pant 20 which, when worn, is positioned on the back of the wearer. The crotch region 26 of the training pant 20 comprises the portion of the training pant 20 which, when worn, is positioned between the legs of the wearer and covers the lower torso of the wearer.

The absorbent chassis 32 further comprises an inner surface 28 which is configured to contact the wearer, and an outer surface 30 opposite the inner surface 28 which is configured to contact the wearer's clothing. As show in FIG. 2, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39, as shown in FIG. 2.

As shown in FIG. 2, the absorbent chassis 32 comprises a rectangular composite structure 33, a pair of transversely opposed front side panels 34, and a pair of transversely opposed back side panels 134. The composite structure 33 comprises a backsheet 40, a topsheet 42 which is connected to the backsheet 40 in a superposed relation, and an absorbent layer 44 which is located between the backsheet 40 and the topsheet 42. For reference, arrow 48 and arrow 49, depicting the orientation of the longitudinal axis and the transverse axis, respectively, of the training pant 20 are illustrated in FIG. 2.

The absorbent chassis 32 is configured to contain and/or absorb any body exudates discharged from the wearer. In accordance with one embodiment of this invention, the absorbent chassis 32 comprises a structure 50 disposed within the crotch region 26 adapted or suitable for opening a support channel 52 adjacent the gluteal fold of the wearer, as representatively shown in FIG. 2. The support channel 52 is configured to help reduce leaks by collecting and transporting fecal material from the target area to regions of the training pant 20 with increased capability of absorbing and containing such material.

Figure 3:
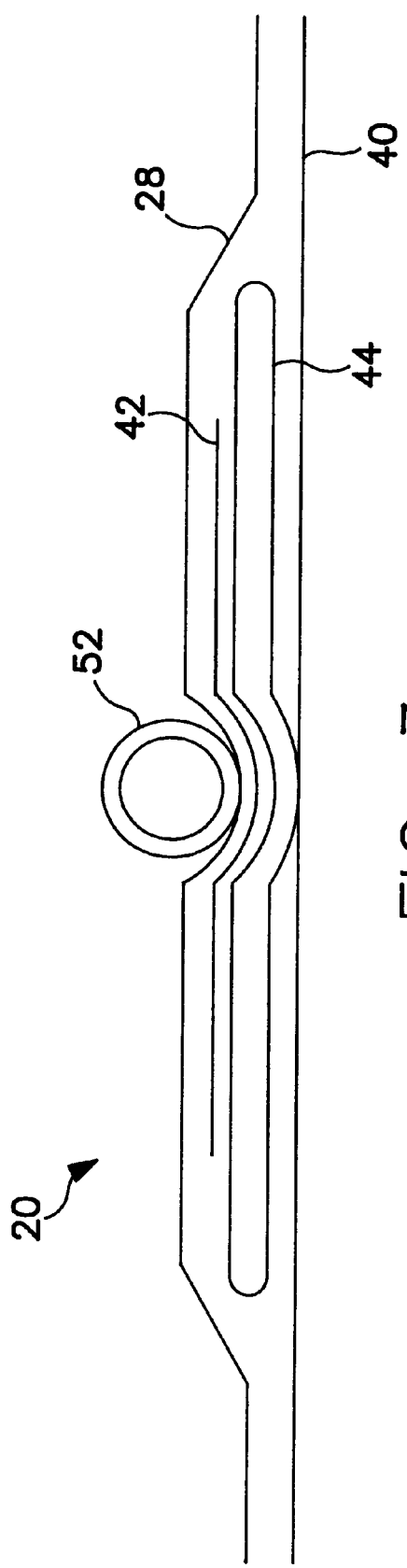
FIG. 3 is a representative side view of a child's training pant in a flat, uncontracted state, in accordance with one embodiment of this invention.

Desirably, the structure 50, having at least one opening for fecal material transport, is positioned on the inner surface 28 of the absorbent chassis 32 between the topsheet 42 and the wearer, as shown in FIG. 3. The structure 50 may remain substantially unattached to the topsheet 42 or may be attached to the topsheet 42 using conventional means, such as adhesives. Desirably, the structure 50 is secured to the topsheet 42 in a manner which stabilizes the structure 50 and maintains the structure 50 in a proper position during use. In this embodiment, the support channel 52 contains and isolates the fecal material which is prevented by the topsheet 42 from penetrating into the absorbent chassis 32. The structure 50 may be partially disposed within the topsheet 42 and/or between the topsheet 42 and the absorbent layer 44.

The structure 50 comprises an expandable element 54 which transitions into or is hingedly connected to a compressible element 56, as shown in FIG. 2. Desirably, the expandable element 54 is hingedly connected with the compressible element 56 in such a way that when the compressible element 56 is compressed, the expandable element 54 expands to form or open the support channel 52.

When the training pant 20 is positioned properly on the wearer, the compressible element 56 is adjacent an ischia area of the wearer, when the wearer is in a sitting position. The term "ischia area" refers to the area corresponding to at least one ischium, referring to the lower portion of an innominate bone, generally on which the body rests when in a sitting position. When the wearer is in a sitting position, the expandable element 54 is within a target area, and desirably the support channel 52 lies along a longitudinal centerline of the training pant 20, adjacent the gluteal fold. The term "target area" generally refers to the area corresponding to that portion of the training pant 20 which is configured to directly receive the insult of fecal exudates from the wearer, and generally is located in the crotch region 26 when the training pant 20 is positioned properly on the wearer.

The support channel 52 may have any shape which provides the desired collection and transport of the fecal material. In accordance with one embodiment of this invention, the support channel 52 has a generally semi-circular or arcuate-shaped cross-section formed by a plurality of lateral support arms 57, as shown in FIG. 2, which traverse the gluteal fold. The support channel 52 alternatively may have a generally tubular or coiled configuration with a generally circular cross-section, a triangular configuration or a semi-triangular configuration with curved sides to provide improved fit within the gluteal fold.

In this embodiment, the expandable element 54 comprises a frame 55 having the lateral support arms 57. When the wearer is in a sitting position, the pressure exerted by the ischia area on the compressible element 56 compresses the compressible element 56. As a result, the expandable element 54 expands and the lateral support arms 57 billow or bend to form the support channel 52, having a generally semi-circular or arcuate-shaped cross-section. The support channel 52 is formed along the longitudinal centerline of the training pant 20. In an expanded configuration, the support channel 52 provides sufficient void space for fecal transport and containment. Desirably, the support channel 52 has a cross-sectional area of at least 0.05 inches$^2$ and a diameter of about 0.25 inch to about 0.75 inch. Upon removal of the compression force, for example when the wearer gets up from the sitting position, the compressible element 56 and the expandable element 54 return to their original shape and the support channel 52 closes. The closed support channel 52 contains and manages body exudates in an isolated region of the absorbent chassis 32 to prevent migration and leakage. Further, with the support channel 52 in a closed configuration, the structure 50 has a minimal thickness and minimal visibility through the training pant 20.

Figure 4:
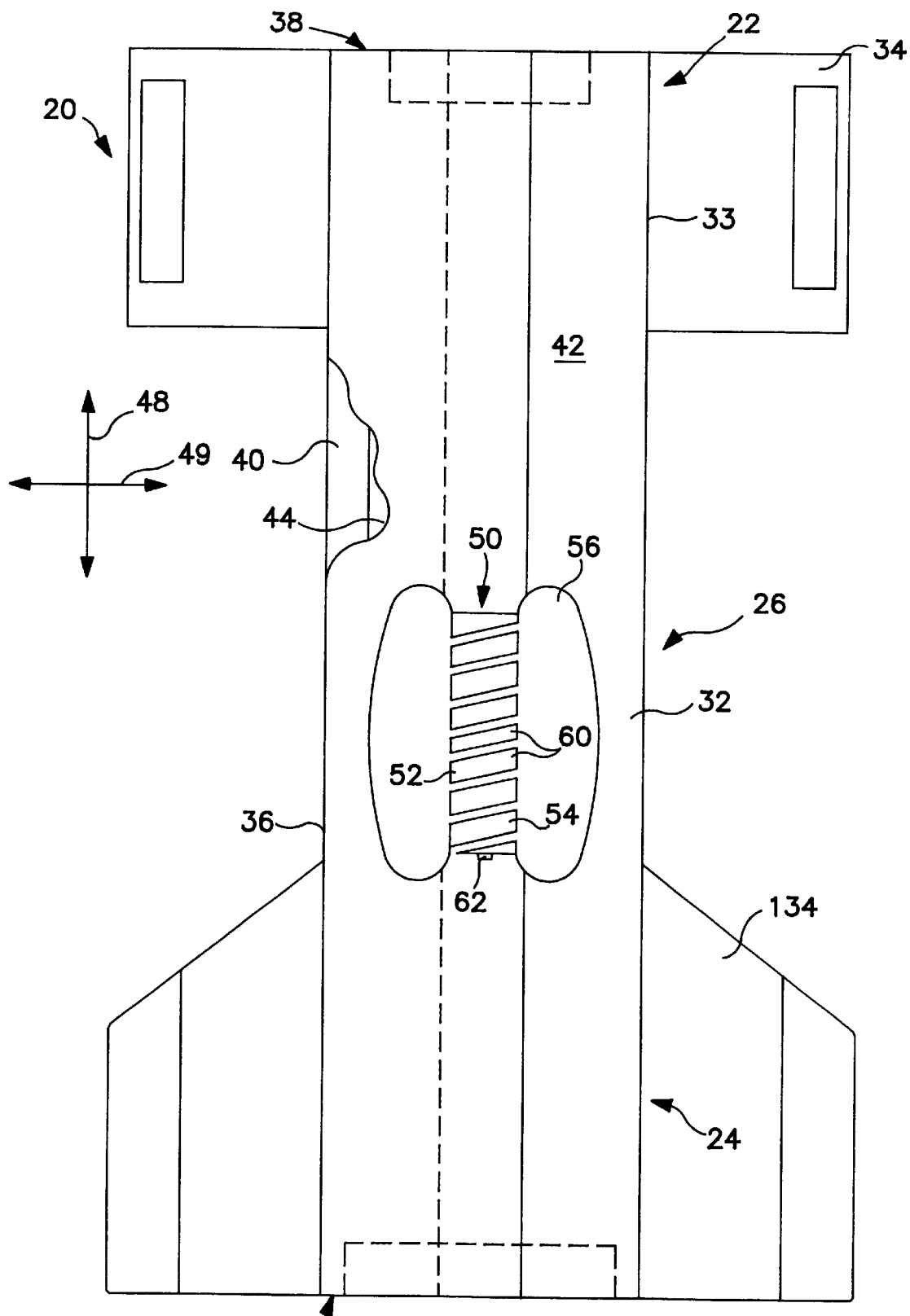
FIG. 4 is a representative plan view of a child's training pant in a flat, uncontracted state, having a structure with a plurality of rib extensions, in accordance with one embodiment of this invention.

In accordance with one embodiment of this invention, the expandable element 54 comprises a plurality of rib extensions 60, as shown in FIG. 4. The rib extensions 60 extend transversely across the gluteal fold from a frame 62 to apply a pressure sufficient to separate the buttocks as the expandable element 54 expands to form the support channel 52, whereby the void space is created for fecal transport and containment.

Desirably, each rib extension 60 has a thickness of about 0.025 inch to about 0.15 inch, more desirably each rib extension 60 has a thickness of about 0.05 inch to about 0.10 inch. Desirably, each rib extension 60 has a length of about 0.1 inch to about 0.7 inch, more desirably each rib extension 60 has a length of about 0.3 inch to about 0.5 inch. Each rib extension 60 may have any thickness and/or length suitable for providing sufficient void space for fecal transport and containment.

Desirably, the support channel 52 is capable of resisting any z-directional compressive forces which may be exerted by the wearer during use. The compressive forces exerted on the support channel 52 are minimized by positioning the support channel 52 adjacent the gluteal fold. However, it is desirable that the support channel 52 is resistant to compression despite the minimal compression forces encountered during use. In accordance with one embodiment of this invention, the support channel 52 has a z-directional compression resistance of at least about 25 percent, desirably at least about 50 percent, and more desirably at least about 70 percent. The compression resistance of the support channel 52 is measured using the Compression Resistance Test discussed below. If the support channel 52 has a compression resistance less than these values, the support channel 52 may collapse during use which adversely affects the ability of the support channel 52 to collect, contain and transport the fecal material. Conversely, if the compression resistence is too high, the support channel 52 may cause undesirable redmarking and/or irritation to the skin of the wearer.

Desirably, the structure 50 comprises a polymer having a high material memory. The term "memory" refers to a material's ability to retain its original configuration upon termination of a deforming force. The structure 50 can be formed from a wide variety of high memory polymers. Suitable polymers include, without limitation, block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Co. under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Certain elastomeric single-site or metallocene-catalyzed olefin polymers and copolymers are also suitable for the structure 50.

In accordance with one preferred embodiment of this invention, at least a portion of the structure 50, for example the compressible element 54 and the frame 62, is covered with a cover material (not shown) to provide softness and comfort to the absorbent chassis 32. Suitable cover materials well known to those having ordinary skill in the art include, but are not limited to, absorbent batts, fibers, and foams.

The absorbent layer 44 can be any structure which is generally compressible, conformable, non-irritating to the wearer's skin, and capable of absorbing and retaining liquids and certain body exudates, for example SAM/fluff batts, compressed cellulose, foam structures, and the like.

In accordance with one embodiment of this invention, the absorbent layer 44 can be manufactured in a wide variety of sizes and shapes, and from a wide variety of liquid absorbent materials commonly used in the art. For example, the absorbent layer 44 can suitably comprise a matrix of hydrophilic fibers, such as a web of cellulosic fluff, mixed with particles of a high-absorbency material commonly known as superabsorbent material. In a particular embodiment, the absorbent layer 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fiber and natural fibers. The superabsorbent particles can be substantially homogeneously mixed with the hydrophilic fibers or can be nonuniformally mixed. The fluff and superabsorbent particles can also be selectively placed into desired zones of the absorbent layer 44 to better contain and absorb body exudates. The concentration of the superabsorbent particles can also vary through the thickness of the absorbent layer 44. Alternatively, the absorbent layer 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefild, Federal Republic of Germany. Typically, a superabsorbent material is capable of absorbing at least 15 times its weight in water, and desirably is capable of absorbing more than 30 times its weight in water.

In one embodiment, the absorbent layer 44 is generally rectangular in shape, and comprises a blend of wood pulp fluff and superabsorbent material. The absorbent layer 44 may have other suitable shapes. For instance, the absorbent layer 44 may have an angular or tapered configuration to better conform to the wearer's body. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent layer 44 in an amount of from about 5 to about 90 weight percent based on a total weight of the absorbent layer 44. The absorbent layer 44 suitably has a density within the range of about 0.10 to about 0.35 grams per cubic centimeter. The absorbent layer 44 may or may not be wrapped or encompassed by a suitable tissue wrap to maintain the integrity and/or shape of the absorbent layer 44.

The topsheet 42 contacts the skin of the wearer while the training pant 20 is worn and prevents substantial contact of the absorbent layer 44 with the skin of the wearer. The topsheet 42 desirably has soft drape characteristics and good fluid penetration properties while maintaining a dry feel and clothlike aesthetics. The topsheet 42 can be treated to be hydrophilic, to more readily transport body exudates to the absorbent layer 44.

A suitable topsheet 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the topsheet 42. For example, the topsheet 42 can be composed of a meltblown or spunbond web of polyolefin fibers. The topsheet 42 can also be a bonded-carded web composed of natural and/or synthetic fibers. The topsheet 42 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Penn. in an active ratio of 3:1. The surfactant can be applied by any conventional means, such as spraying, printing, brush coating or the like. The surfactant can be applied to the entire topsheet 42 or can be selectively applied to particular sections of the topsheet 42, such as the medial section along the longitudinal centerline.

A suitable liquid permeable topsheet 42 is a nonwoven bicomponent web having a basis weight of about 1 to about 100 grams per square meter (gsm), suitably about 20 to about 40 gsm, more suitably about 27 gsm. The nonwoven bicomponent web can be a spunbond bicomponent web, or a bonded-carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the backsheet 40 and the topsheet 42 can comprise elastomeric materials, it can be desirable in some embodiments for the composite structure to be generally inelastic, where the backsheet 40, the topsheet 42 and the absorbent layer 44 comprise materials that are generally not elastomeric.

The backsheet 40 desirably comprises a material that is substantially liquid impermeable, and can be elastic, stretchable or nonstretchable. The backsheet 40 can be a single layer of liquid impermeable material, but desirably comprises a multi-layered laminate structure in which at least one of the layers is liquid impermeable. For instance, the backsheet 40 can include a liquid permeable outer layer and a liquid impermeable inner layer that are suitably joined together by a laminate adhesive. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably is one that provides a generally cloth-like texture. One example of such a material is a 20 gsm spunbond polypropylene nonwoven web. The outer layer may also be made of those materials of which the liquid permeable topsheet 42 is made. While it is not a necessity for the outer layer to be liquid permeable, it is desired that it provides a relatively cloth-like texture to the wearer.

The inner layer and the outer layer can be both liquid and vapor impermeable, or can be liquid impermeable and vapor permeable. The inner layer is desirably manufactured from a thin plastic film, although other flexible liquid impermeable material may also be used. The inner layer, or the liquid impermeable outer cover when a single layer, prevents waste material from wetting articles, such as bedsheets and clothing, as well as the wearer and caregiver. A suitable liquid impermeable film for use as a liquid impermeable inner layer, or a single layer liquid impermeable outer cover, is a 0.02 millimeter polyethylene film commercially available from Huntsman Packaging of Newport News, Va., U.S.A. If the outer cover is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc. Tokyo, Japan, or an XKO-8044 polyolefin film commercially available from 3M Company, Minneapolis, Minn., U.S.A.

Compression Resistance Test

This test is configured to measure the compression resistance of materials intended for use as the support channel 52 according to the present invention. The compression resistance of the materials indicates the ability of the material to maintain its shape during use.

A sample of the material intended for use as the support channel 52 is obtained. The compression resistance of the material is tested in a standard compressometer such as that commercially available from Frazier Precision Instrument Company, a business having offices located in Gaithersburg, Md. Initially, the compressometer is calibrated. The sample of material is then placed in the compressometer which includes a foot which defines a diameter of 3.0 inches. The foot is positioned in contact with the sample of material and the original height of the material is measured and recorded. The foot is then lowered until the pressure on the material is 1.0 pound per square inch. The compressed height of the material is immediately measured and recorded. The compression resistance value of the material sample is then obtained by dividing the compressed height by the original height and multiplying the result by 100 percent.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A personal care absorbent article comprising:
    a front region, a back region and a crotch region intermediate the front region and the back region; and
    a structure disposed in said crotch region and positioned on an inner surface of said personal care absorbent article between a topsheet and a wearer suitable for opening a support channel in a gluteal fold when the wearer of said personal care absorbent article is in a sitting position, said structure comprises an expandable element connected to a compressible element whereby said expandable element expands to form said support channel upon compression of said compressible element, wherein said expandable element comprises a frame having a plurality of lateral support arms adapted to traverse the gluteal fold.

2. A personal care absorbent article in accordance with claim 1, wherein said structure comprises a material selected from the group consisting of block copolymers of polystyrene, polyisoprene and polybutadiene; copolymers of ethylene, natural rubbers and urethanes; copolymers of ethylene, including without limitation, ethylene vinyl acetate, ethylene methyl acrylate, ethylene ethyl acrylate, ethylene acrylic acid, stretchable ethylene-propylene copolymers, and combinations thereof; elastomeric single-site or metallocene-catalyzed olefin polymers and copolymers; and combinations thereof.

3. A personal care absorbent article in accordance with claim 1, wherein said support channel has a compression resistance of at least about 25 percent.

4. A personal care absorbent article in accordance with claim 1, wherein said support channel has a compression resistence of at least about 50 percent.

5. A personal care absorbent article in accordance with claim 1, wherein said support channel has a compression resistance of at least about 70 percent.

6. A personal care absorbent article in accordance with claim 1, wherein said expandable element comprises a frame having a plurality of rib extensions.

7. A personal care absorbent article in accordance with claim 6, wherein each rib extension has a thickness of about 0.025 inches to about 0.15 inches.

8. A personal care absorbent article in accordance with claim 6, wherein each rib extension has a thickness of about 0.05 inches to about 0.10 inches.

9. A personal care absorbent article in accordance with claim 6, wherein each rib extension has a length of about 0.1 inches to about 0.7 inches.

10. A personal care absorbent article in accordance with claim 6, wherein each rib extension has a length of about 0.3 inches to about 0.5 inches.

11. A personal care absorbent article in accordance with claim 1, wherein said support channel has a cross-sectional area of at least 0.05 inches$^2$.

12. A personal care absorbent article in accordance with claim 1, wherein said support channel has a diameter of about 0.25 inches to about 0.75 inches.

13. A personal care absorbent article in accordance with claim 1 comprising a diaper.

14. A personal care absorbent article in accordance with claim 1 comprising training pants.

15. A personal care absorbent article in accordance with claim 1 comprising absorbent underpants.

16. A personal care absorbent article in accordance with claim 1, wherein at least a portion of said structure is covered with a cover material.

17. A personal care absorbent article in accordance with claim 16, wherein said cover material comprises a material selected from the group consisting of an absorbent batt, a fiber, a foam and combinations thereof.

18. In a personal care absorbent article having a front region, a back region and a crotch region intermediate the front region and the back region, the improvement comprising:
    a structure disposed in said crotch region and positioned on an inner surface of said personal care absorbent article between a topsheet and a wearer suitable for opening a support channel in a gluteal fold having a compressible element and an expandable element connected to said compressible element, said expandable element expandable to form said support channel upon compression of said compressible element, and comprising a frame having a plurality of rib extensions,
    wherein said plurality of rib extensions extend transversely across the gluteal fold.

* * * * *